United States Patent [19]
Fullemann

[11] Patent Number: 5,531,810
[45] Date of Patent: Jul. 2, 1996

[54] INJECTION SEPTUM WITH DUST WIPER

[75] Inventor: James S. Fullemann, Half Moon Bay, Calif.

[73] Assignee: Merlin Instrument Company, Half Moon Bay, Calif.

[21] Appl. No.: 310,276

[22] Filed: Sep. 21, 1994

[51] Int. Cl.$^6$ .................................................... B01D 15/08
[52] U.S. Cl. ......................... 96/105; 210/198.2; 215/247; 215/310
[58] Field of Search .................. 96/101–107; 210/198.2; 215/247, 292, 307, 310

[56] References Cited

U.S. PATENT DOCUMENTS

| | | | |
|---|---|---|---|
| 4,954,149 | 9/1990 | Fullemann | 55/386 |
| 4,969,938 | 11/1990 | America | 96/106 X |
| 5,193,703 | 3/1993 | Staats, III et al. | 96/106 X |
| 5,338,448 | 8/1994 | Gjerde | 96/102 X |

FOREIGN PATENT DOCUMENTS 1525794  7/1970  Germany .................................. 96/101

OTHER PUBLICATIONS

JADE Valve advertisement, date unknown.

*Primary Examiner*—Robert Spitzer
*Attorney, Agent, or Firm*—Anderson & Hirsch

[57] ABSTRACT

A cap assembly for a gas chromatography injection port includes a two-piece septum. The two-piece septum includes a syringe seal for sealing an injection needle and a duckbill seal for sealing the injection port when the needle is not inserted. The syringe seal includes three annular ribs in its aperture. At the aperture base is a sealing rib that provides the main sealing function for the syringe seal. Just above the sealing rib is a stress-relief rib. At the top of the aperture is a wiping rib. The wiping rib wipes dust on the needle exterior so that it does not enter the aperture. Dust entering the aperture can be retained in the relatively large dust pocket between the wiping rib and the strain-relief rib. The septum is held in place by a septum nut that has a recess above the wiping rib for holding dust removed from the needle by the wiping rib. A washer in the recess prevents the syringe seal from deforming into the recess. The septum nut includes a guide aperture section that aligns the syringe needle with the apertures of the syringe seal and the duckbill seal. The septum nut is made of anodized aluminum to provide ready machinability for formation of the guide aperture section and sufficient hardness to resist damage inflicted by the syringe needle.

5 Claims, 7 Drawing Sheets

INJECTION SEPTUM WITH DUST WIPER

BACKGROUND OF THE INVENTION

The present invention relates to chromatography systems used for chemical analysis and, more particularly, to an improved septum for an injection port of a gas chromatography system.

In gas chromatography, samples are separated into their components by passing the sample through a separating column. The sample is introduced into a flowing carrier gas in an injection port. The carrier gas sweeps the sample from the injection port into the separating column. The separated components emerging from the column are eluted through a detector that monitors the elution over time. A chromatogram, representing eluting quantity as a function of time, is generated by plotting the detector output signal.

Typically, the carrier gas is sealed from the outside world by a rubber septum. The sample is introduced into the injection port using a syringe that pierces the septum. The sample is injected into the inlet system and the syringe needle is withdrawn.

The septum must serve two functions. First, it must form a seal around the needle to prevent leaks while the injection is effected. Second, it must reseal the injection port after the syringe needle has been withdrawn and maintain this seal while the chromatographic separation is being executed. A leak occurring while the needle is in the septum can cause part of the injected sample to escape the injection system. This "injection" leak is difficult to detect because it occurs during the dynamic process of injection and is only apparent by careful examination of the quantitative results of the chromatogram. A failure to seal after the needle is withdrawn is more easily detected. The resulting "post-injection" leak is evident from variations in the characteristic retention time for a chromatographic peak resulting from variations in the column flow rate. Some capillary column injection ports may show different behavior for a post-injection leak because of their flow configuration.

Septum deterioration and resulting failure are serious problems. Monitoring a system for leaks can be costly and time consuming. Replacement of seals is inconvenient. Problems of detection and replacement are aggravated in automated systems which may run unattended for as many as 100 samples. A failure early in a run can impair the validity of the results for all subsequent samples.

Septum deterioration is inevitable due to the action of the syringe needles used for injection. Syringe needles must be strong enough to pierce the septa of sample containers and injection ports without bending or buckling. This strength requirement leads to the use of larger diameter needles. Larger diameter needles require greater insertion force to pierce a septum, which is thus subject to greater wear. The larger needles also make larger holes or tears in the septum, which are harder to reseal after needle withdrawal. Needles of smaller diameter cause less damage to the septum and make resealing easier, but are much more susceptible to bending when piercing a seal.

Syringe needles are made with sharp, beveled points to slice through the septa with lower force. However, the slicing action of repeated injections with beveled needles can lacerate a septum, which then begins to leak. In addition, small pieces of rubber torn from a septum by the needles can fall into the injection port liner. Once in the liner, these pieces can affect the analysis in two ways. First, they can release compounds which can appear as "ghost peaks" in the chromatogram. Second, they can adsorb or partition sample components as they pass through the injection port, causing distortion of peak shapes in the chromatogram. In either case, the validity of the resulting chromatogram is impaired.

Taking into account these considerations, most gas chromatographs use a rubber septum, approximately 3 mm thick and 6–12 mm in diameter. Syringes typically used with such septa are 10 microliter total capacity, with a sharp beveled 26 gauge, i.e., 0.48 mm diameter, needle. These are used for both manual injection and for automatic liquid samplers. Alternatively, thicker "cylindrical" septa are used to improve the reliability of sealing after multiple injections. These have the disadvantage of requiring higher syringe force.

Especially strenuous demands are made on a septum in automatic liquid samplers, such as the Hewlett-Packard 7673. This sampler uses a very rapid injection cycle. A differently shaped needle is adapted so that it can pierce a septum, the liquid sample can be injected into the injection port liner, and the needle can be removed from the port in less than 0.25 second before the syringe needle contents can be heated significantly by the injection port or the septum. The needle has a relatively large diameter, e.g., 0.66 mm, to allow it to withstand the higher force required to pierce the septum at high speed without bending or buckling. The needle has a blunt tip which facilitates a properly directed spray pattern for the sample. The larger diameter and blunt tip cause greater damage to the septum per injection, thus shortening the septum life before leaks occur or pieces of septum fall into the injection liner.

The problem of laceration can be addressed by using a septum having a predefined path for needle penetration. For example, septa have been adapted from "duckbill" seals. A duckbill seal comprises a flat rubber tube with two flat surfaces which can seal against each other. Duckbill seals are often used as check valves in flow systems because they open with very low pressure drop in one direction while sealing in the other direction. Duckbill seals are effective under high pressure, which causes the flat surfaces to press against each other more tightly.

Because a slit is preformed between the flat surfaces, a blunt needle can be inserted with low force through a duckbill seal many times without tearing or crumbling the rubber by forcing the flat surfaces apart. However, the flat seals do not form an effective seal about a syringe needle so leaks can occur during injection. In addition, the low pressure drops across the seal can be insufficient to close the flat surfaces, allowing post-injection leaks. The problem with post-injection leaks can be remedied by adding a spring to force the sealing surfaces together.

A duckbill seal has been included in a inlet assembly for a capillary column. For example, in the "*Hewlett-Packard 1988 Analytical Supplies Catalog and Chromatography Reference Guide*", page 35, a "Cool On-Column Inlet" includes a duckbill seal. Inspection of the actual system reveals that a stainless steel probe is used to separate the duckbill surfaces. Once the surfaces are separated by the probe, the needle is extended through the probe and the probe is withdrawn so that the duckbill closes around the needle. Neither the probe nor the duckbill seals the needle completely, so that some leakage generally occurs. It is noted that the inner perimeter of the duckbill seal is about 1.6 mm at the duckbill end and about 3.1 mm at the end where the needle is first inserted, so that this latter end never forms a seal with the needle.

A septum including interlocked syringe and duckbill seals is disclosed in U.S. Pat. No. 4,954,149 to Fullemann. The annular syringe seal prevents leakage during injection by syringe. The duckbill seal prevents fluid leakage after the needle is withdrawn from the septum. A spring clip is used to urge the duckbill closed as the needle is withdrawn to ensure closure even at low pressures. The syringe seal aperture is wider at the top to help guide the needle. This aperture converges to an annular base sealing element, the diameter of which is smaller than the needle to provide a tight seal while the needle is inserted. While a definite improvement over the simple duckbill seal, this hybrid-seal injection septum could leak due to deformation of the base sealing detail of the syringe seal when the needle was misaligned.

An improved interlocked injection septum uses dual annular sealing elements in the syringe seal. An annular sealing element is located at the base of the syringe seal, while an annular strain-relief element is located just above the sealing element. A misaligned needle deforms the guide detail. The deforming force, however, moves the sealing element into alignment with the needle. Thus, the sealing element is not deformed and so is able to form a secure seal against the needle.

This improved interlocked injection septum essentially answered the industry call for a reliable and longer lasting seal. However, once the original objectives were met, the industry raised its sights. After thousands of injections, the dual-detail interlocked injection septa are prone to leakage. What is needed is a similarly effective septum that has a substantially greater mean-time-before-failure (MTBF).

SUMMARY OF THE INVENTION

In accordance with the present invention, the syringe seal of an interlocked syringe/duckbill septum includes at least three annular sealing elements. These elements can be in the form of ribs molded into the wall of a central "syringe" aperture of the syringe seal. One of these elements is located at the base of the aperture and performs the primary sealing function of preventing chromatography gas from leaking through the septum while the needle is inserted; this element is referred to as the "seal element" or, more specifically, as the "sealing rib". Just above the seal element is a strain-relief element, which absorbs stress due to needle misalignment that might otherwise deform the sealing element. A wipe detail is located near the top of the syringe aperture to wipe particles from the needle exterior so that they do not enter the syringe aperture.

The unstressed inner diameters of the sealing elements are slightly less that the nominal diameter of the intended injection needle. When the needle is inserted, these elements forcefully contact the needle to effect their respective functions. Between these elements are pockets of slightly greater diameters. When the needle is inserted, the diameters of these pockets are slightly greater than the needle diameter, allowing room for dust (particles) to collect. There is at least one "seal" dust pocket between the seal element and the strain-relief element, and one "wipe" dust pocket between the wipe element and the strain-relief element. The strain-relief element is substantially closer to the seal element that to the wipe element so that the wipe pocket volume is substantially greater than the seal pocket volume.

This septum can be seated in a septum cup of an injection port of a gas chromatography system. The septum can be held in place by a septum nut. Preferably, this septum nut serves to guide the needle into the syringe aperture so that the syringe seal suffers minimal misalignment stress and tear. To this end, this septum nut can have a guide-nut aperture with an upper capture section and a lower guide section. The guide section can be cylindrical, with a diameter greater than the needle diameter but less than 130% of the needle diameter to limit lateral misalignment. Needle misalignment can be further limited by a high aspect ratio (height/diameter) of the guide section. Preferably, this aspect ratio is at least 2:1.

To facilitate drilling of the high-aspect ratio guide section, the septum nut can be of aluminum. After drilling, the septum nut can be anodized to increase its hardness, and thus its resistance to needle damage.

The capture section of the guide-nut aperture is designed to capture the needle as it is inserted and align it with the guide section. Accordingly, the capture section can be wide at its top and narrow at its bottom. Preferably, the guide section is conical, with diameters subtending an angle of at most 60°. Preferably, the top (maximum) diameter is at least 5–10 times that of the guide section.

The septum nut can be defined with a recess that serves to gather dust removed from the needle by the wiping element. Upon assembly with the septum, volume of this recess not occupied by any part of the septum should be at least the cube of the needle diameter. For a cylindrical recess, the diameter of the recess should be at least twice the needle diameter, while the height of the recess should be at least one needle diameter. Thus, the recess volume is at least the cube of the needle diameter. To maintain this recess volume against deformation of the elastic septum, a washer can be disposed between the septum nut and the syringe seal.

In the course of the present invention, it was determined that the primary cause of failure of the prior art septa with guide and base details was dust that entered the duckbill seal and prevented it from closing completely after the needle was withdrawn. Typically, dust is introduced on the outside of the needle. It initially collects above the guide detail. Continued injections shove this dust into the pocket between the guide and base details. As this pocket fills, further injections drive the dust out of the syringe seal and into the duckbill seal, which suffers due to the presence of dust.

The major advantage of the present invention is greater "mean time between failures" for a septum. This is achieved by inhibiting the entrance of dust into the duckbill seal, which dust can prevent the duckbill seal from closing gas-tight. The wipe element prevents most needle dust from entering the syringe seal aperture, diverting it instead to the septum nut cavity. Dust entering the syringe aperture is maintained in the relatively large wipe pocket. From the wipe pocket, the dust must migrate to the seal pocket before entering the duckbill seal.

Another advantage of the present invention is that the septum nut provides for better alignment of the needle with the syringe aperture. In particular, the high-aspect-ratio guide section of the septum nut provides this better alignment. This guide function is performed by the syringe seal in the prior art. The harder septum nut provides more certain alignment than the elastomeric syringe seal. More importantly, relieving the syringe seal of the alignment function permits incorporation of the wipe element.

The aluminum septum nut of the present invention provides for better machinability than the stainless steel used in prior art septum nuts. This facilitates precise drilling of the high-aspect-ratio guide section, which in turn allows the septum nut to perform its alignment function. These and other features and advantages of the present invention are apparent from the description below with reference to the following drawings.

DESCRIPTION OF THE PREFERRED EMBODIMENTS

Figure 1:
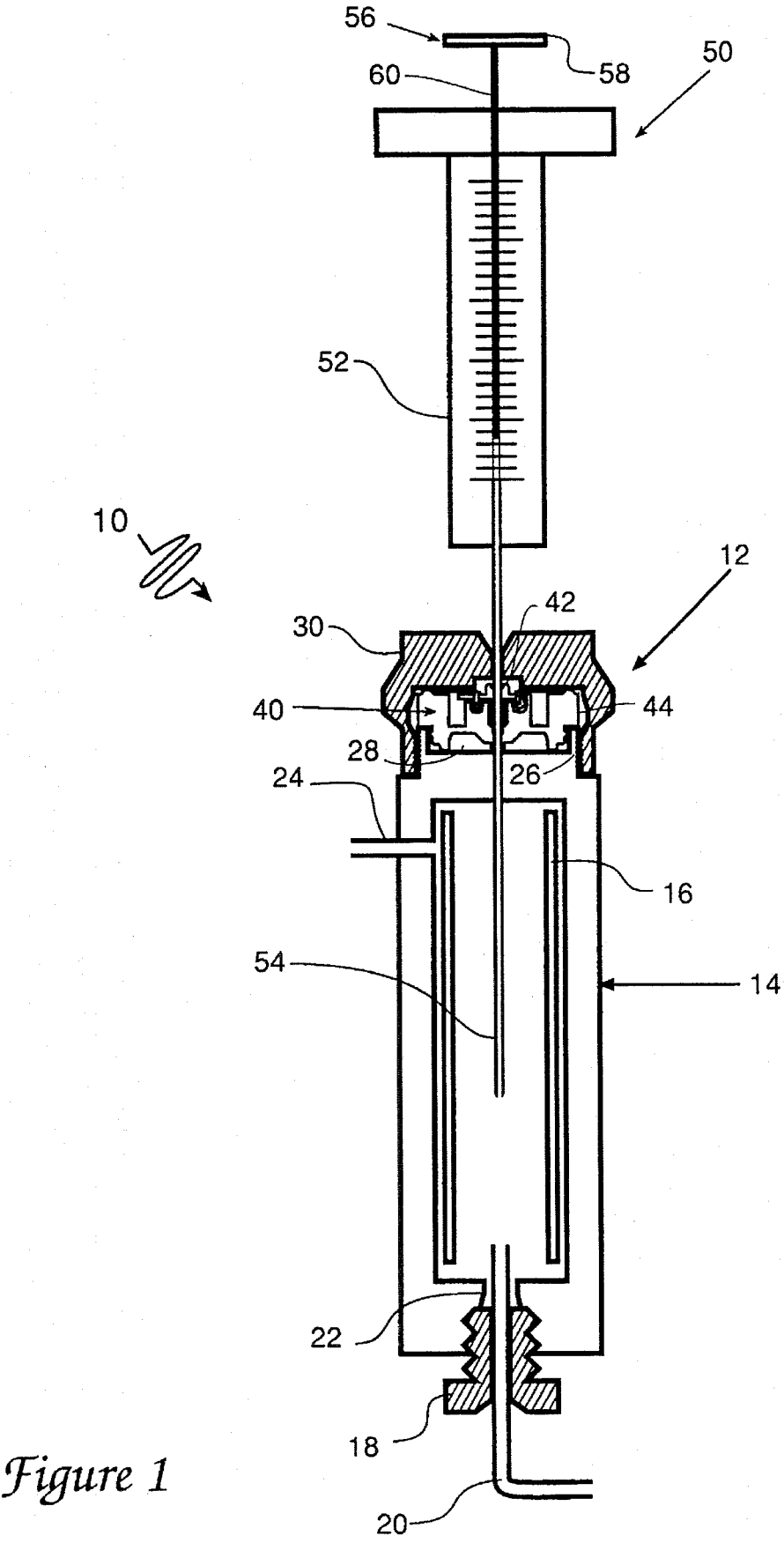
FIG. 1 is a sectional view of an inlet injection port incorporating a septum assembly of the present invention during a step in which fluid is introduced into the port by a syringe.

An injection port 10 for a gas chromatography system is shown in FIG. 1 during sample injection. Injection port 10 comprises a septum assembly 12, a body 14, a liner 16, and a column nut 18. Column nut 18 secures an end of a separation column 20 where it extends through an outlet 22 in the base of body 14. Body 14 has a carrier gas inlet 24. Body 14 includes an externally (male) threaded annular ridge 26 that defines a septum cup 28 to its radial interior.

Figure 2:
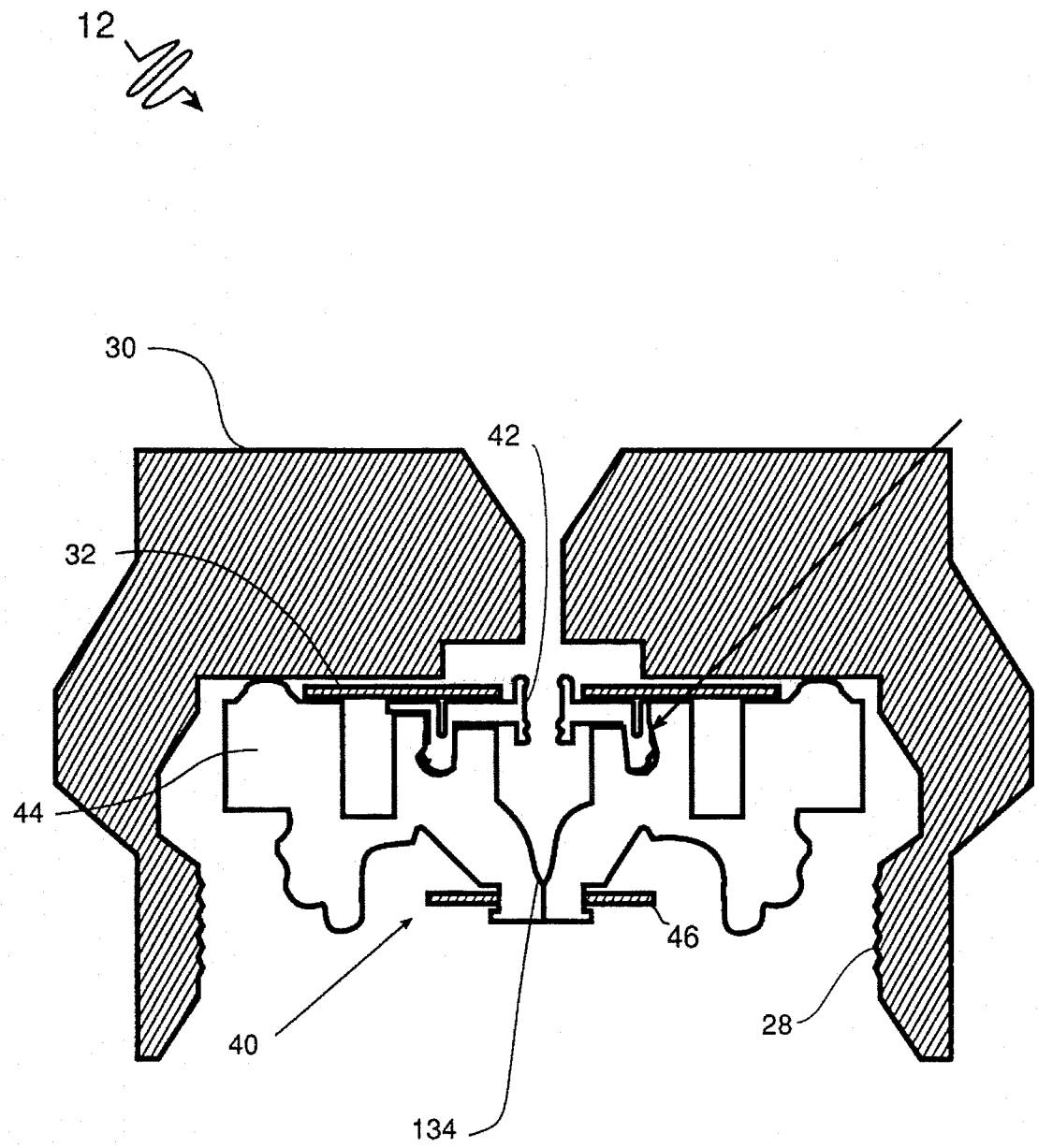
FIG. 2 is a sectional view of the septum assembly of FIG. 1.

Septum assembly 12 includes a septum nut 30, a washer 32, and a septum 40, as best seen in FIG. 2. Septum 40 includes a syringe seal 42, a duckbill seal 44, and a clip 46. Septum 40 is seated in septum cup 28, as shown in FIG. 1. Septum nut 30 is female threaded and mated to ridge 26 so that, with the cooperation of washer 32, it holds septum 40 in place.

Injection port 10 is used for injecting sample into gas separation column 20, shown in FIG. 1. Sample is delivered by a syringe 50 that includes a graduated cylinder 52, a relatively blunt and cylindrically symmetrical needle 54, and a plunger 56, as shown in FIG. 1. Plunger 56 includes a plunger cap 58 and a piston 60. Needle 54 is relatively blunt to minimize piercing or slicing of septum 40.

When sample is ejected from syringe 50 into injection port 10, carrier gas flowing in through inlet 24 forces sample into column 20. Backflow through septum 40 is prevented during injection by a secure seal between needle 54 and syringe seal 42. After needle 54 is withdrawn, clip 46 forces duckbill seal 44 closed, again preventing sample backflow.

Figure 3:
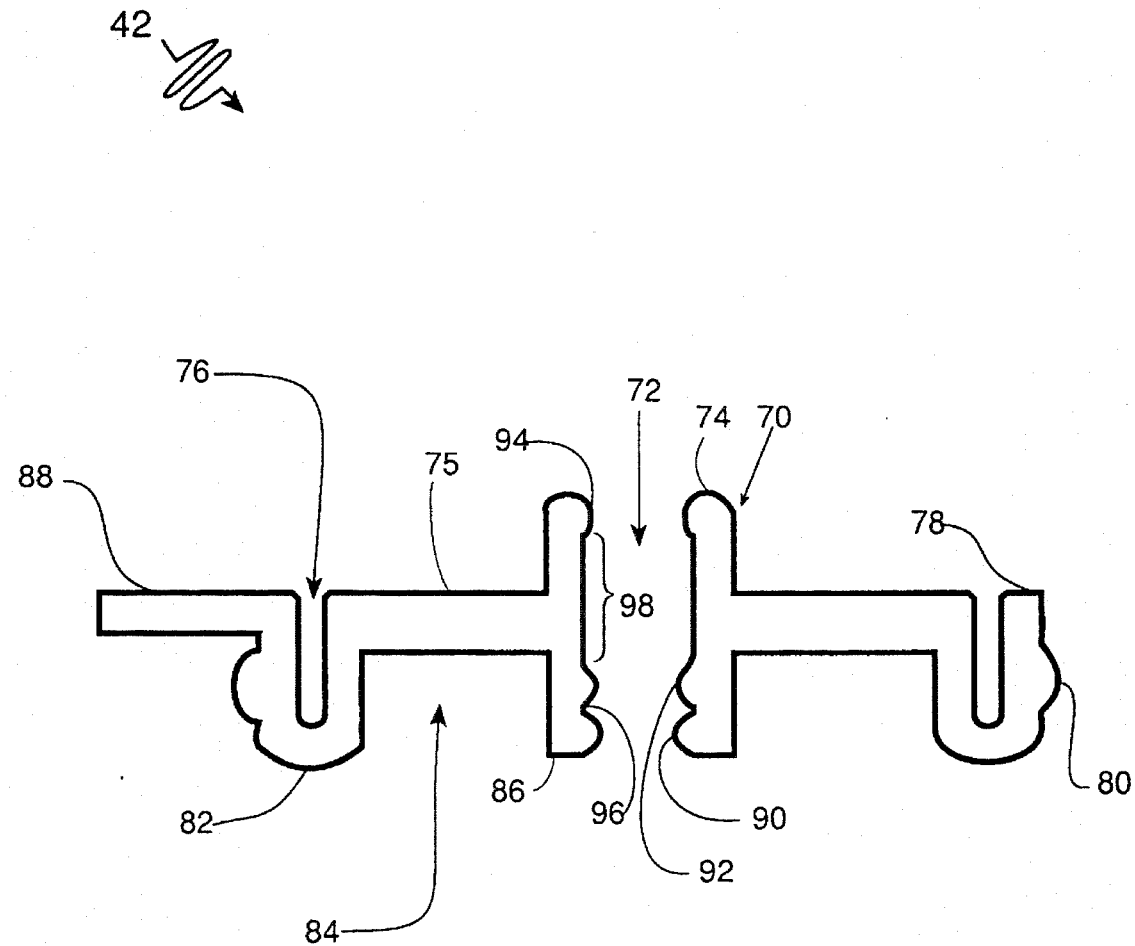
FIG. 3 is a sectional view of a syringe seal of the septum of FIG. 1.

Syringe seal 42 is designed to provide a sliding seal around syringe needle 54 during the injection process. As shown in FIG. 3, syringe seal 42 has axial symmetry and includes central annular aperture wall 70 defining a syringe-seal aperture 72, an upper lip 74, an upper ledge 75, a narrow upper groove 76, an upper rim 78, an annular outer rib 80, a lower rim 82, a wide lower groove 84, and a lower lip 86. A flap 88 extends to one side of upper rim 78 to serve as a handle for removal of syringe seal 42 from septum 40; such removal is recommended for periodic washing or ultrasonic cleaning. Aperture wall 70 extends from the top of upper lip 74 to the base of lower lip 86.

Aperture wall 70 includes three ribs that actually contact syringe needle 54 during insertion; these ribs are sealing rib 90, strain-relief rib 92, and wiping rib 94. In fact, each rib seals, provides strain relief, and wipes; nevertheless, the rib labels indicate the appropriate functional emphasis for the ribs.

Sealing rib 90 serves as the primary seal when a needle is inserted through septum 40. This rib corresponds to the base of the annular web of the syringe seal described in U.S. Pat. No. 4,954,149. In that seal, the aperture widens toward the top, so that the annular web base is the only part of the seal to contact a properly inserted needle. A problem with that design is that when the needle is inserted off axis, the resulting stress deforms the seal where it contacts the needle. This distortion can lead to a lack of conformance of seal to needle, causing leakage.

An intermediate design uses a sealing rib at the base of the syringe seal aperture and adds a strain-relief rib slightly above the sealing rib. The strain-relief fib absorbs most of the stress induced by an off-axis needle. As a result, the sealing rib seals against the needle without distortion. An unintended consequence of the addition of the strain-relief rib was the formation of a dust pocket between the strain-relief rib and the sealing rib. The strain-relief rib and the dust pocket correspond to strain-relief rib 92 and lower dust pocket 96 of syringe seal 42.

Durability studies of the intermediate septum with two inner ribs indicated that dust was the primary cause of failure. Small particles would gradually make their way through the syringe seal and lodge themselves in the slit of the duckbill seal, which could then fail to close. The present invention is designed to extend the septum lifetime by prolonging the time before such a failure is likely to occur.

To this end, wiping rib 94 is added near the top of syringe seal 42. The main function of wiping rib 94 is to prevent dust from entering septum 40 in the first place. The addition of the wiping rib defines an upper dust pocket 98. Strain-relief rib 92 is much closer to sealing rib 90 than to wiping rib 94 so that dust pocket 98 is larger than dust pocket 96. Dust that does enter septum 40 can reside in dust pocket 98 for a relatively long time before migrating to lower dust pocket 96 and to duckbill seal 44.

Some stretching of ribs 90, 92, and 94 is desired to provide a snug seal against needle 54. Accordingly, the inner diameters of ribs 90, 92, and 94 are selected to be 0% to 30%, preferably 15%, smaller than the target injection needles. Also accordingly, syringe seal 42 is made of elastomeric material, preferably molded rubber.

Rib 80 is used for interlocking with duckbill seal 44 when syringe seal 42 is inserted into duckbill seal 44 using a tubular insertion tool. Narrow upper groove 76 receives the tubular insertion tool for septum assembly. In addition, groove 76 and rib 80 define a spring that permits rim 78, along with rib 80, to contract radially as syringe seal 42 is snapped into position in duckbill seal 44. When the insertion tool is removed, rim 78 and rib 80 expand radially to effect interlocking of seals 42 and 44 as shown in FIG. 2.

Figure 4:
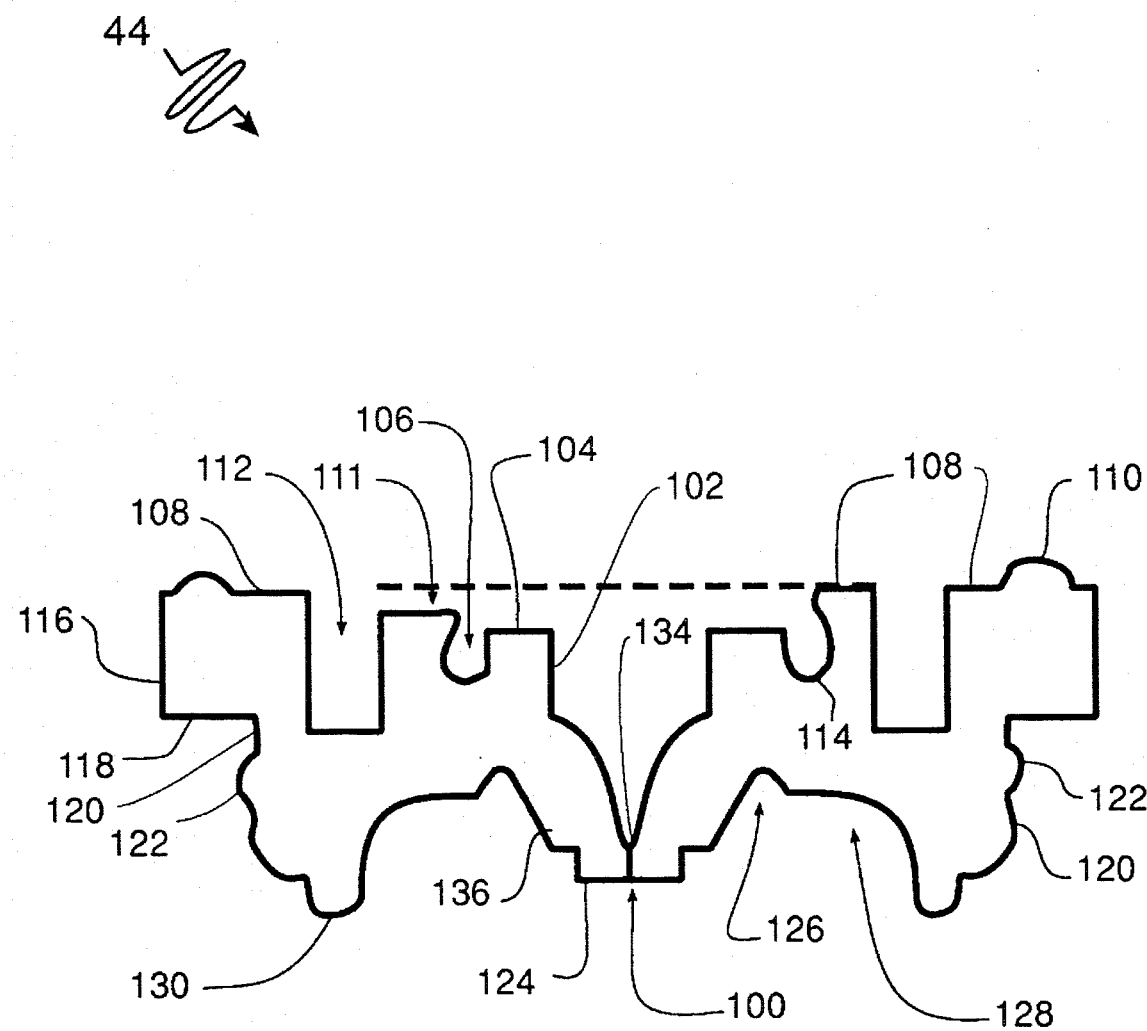
FIG. 4 is a sectional view of a duckbill seal of the septum of FIG. 1 taken along the same line as FIG. 1.

Duckbill seal 44 is designed to provide a pressure seal for injection port 10 while syringe needle 54 is not inserted. Like syringe seal 42, duckbill seal 44 is made of elastomeric material, preferably molded rubber. As shown in FIG. 4, duckbill seal 44 includes, from top center radially outward, a duckbill aperture 100, an annular upper seat 102, an annular upper-inner ridge 104, an annular upper groove 106, an annular flange 108, and an annular upper-outer rib 110. Upper-outer ridge 108 includes a flap recess 111 for receiving flap 88 of syringe seal 42. Outer alignment holes 112 provide for handling of duckbill seal 44 during slit formation, as described below.

These features are dimensioned to receive syringe seal 42 as shown in FIG. 2. Seat 102 is large enough to admit the lower lip 86 of syringe seal 42 and allow it lateral movement to accommodate needle misalignment. Upper inner ridge 104 mates with wide lower groove 84 of syringe seal 42; upper groove 106 mates with lower rim 82 of syringe seal 42. In addition, upper groove 106 includes a lateral groove 114 which mates with rib 80 of syringe seal 42. Flange 108 serves as a seat for washer 32. Upper outer rib 110 centers washer 32. Rib 110 also serves as a stop for septum nut 30 as it is threaded onto body 14, and provides a seal against septum nut 30.

Side features of duckbill seal 44 include, from top to bottom, a flange sidewall 116, a flange base 118, a lower sidewall 120, and an outer rib 122, as shown in FIG. 4. Duckbill seal 44 is compressed due to pressure applied when septum nut 30 is threaded into place. With duckbill seal 44 is so compressed, flange base 118 and outer rib 122 seal against septum cup 28. Rib 122 also helps center septum 40 within septum cup 28 before septum nut 30 is threaded into position.

Bottom features of duckbill seal 44 include, from center radially outward, lips 124, annular deep lower groove 126, annular shallow lower recess 128, and annular lower rim 130, as shown in FIG. 4. Recess 128 accommodates clip 46, while rim 130 prevents escape of clip 46.

Duckbill lips 124 are flexible to accommodate needle misalignment. Lips 124 are tapered at an angle of 75°. A slit 132, shown in FIG. 5, defines the base of duckbill aperture 100. Alignment holes 112 provide for placement of duckbill seal 44 on an alignment fixture so that slit 132 is properly oriented. The inner surface of lips 124 is tapered so that duckbill aperture 100 is wedge shaped, terminating in a more blunt taper 134, with an angle of about 90°, at slit 132, as seen in FIG. 5.

Figure 5:
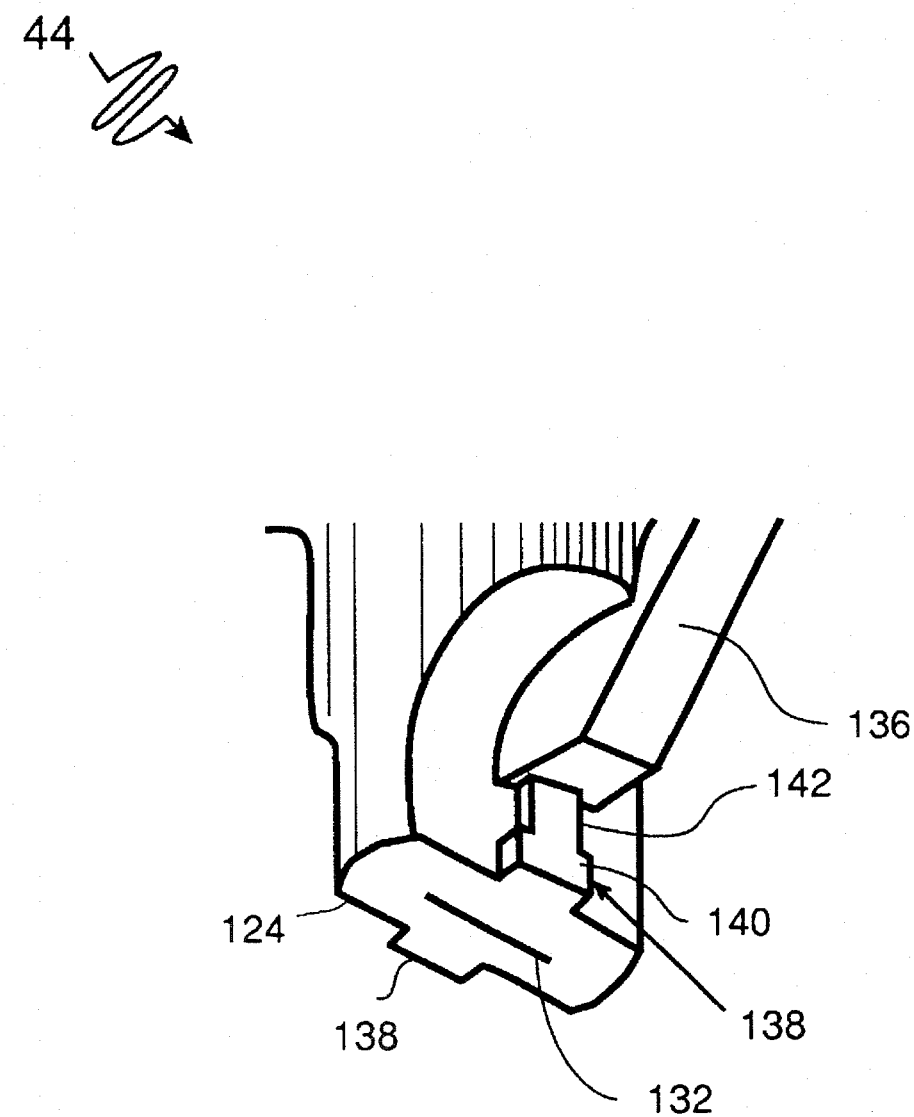
FIG. 5 is a perspective cutaway view of the duckbill seal of FIG. 4.

On the outside of lips 124 are an opposing pair of linear reinforcements 136 and a pair of inverted "T" structures 138, as indicated in FIGS. 4 and 5. Each inverted "T" structure 138 includes a base 140 and a stem 142, as shown in FIG. 5. Stems 142 engage clip 46, while bases 140 and reinforcements 136 confine its vertical movement. Reinforcement 136 also acts as a guide when clip 46 is engaged. Reinforcement 136 is designed to limit distortion of lips 124 during high pressure when needle 54 is not inserted. Lips 124 prevent fluid leakage of pressurized gas in injection port 10 through the septum aperture. Fluid pressure in lower groove 126 and recess 128 tends to force septum 40 to expand against septum cup 28, providing sealing about septum 40.

Figure 6:
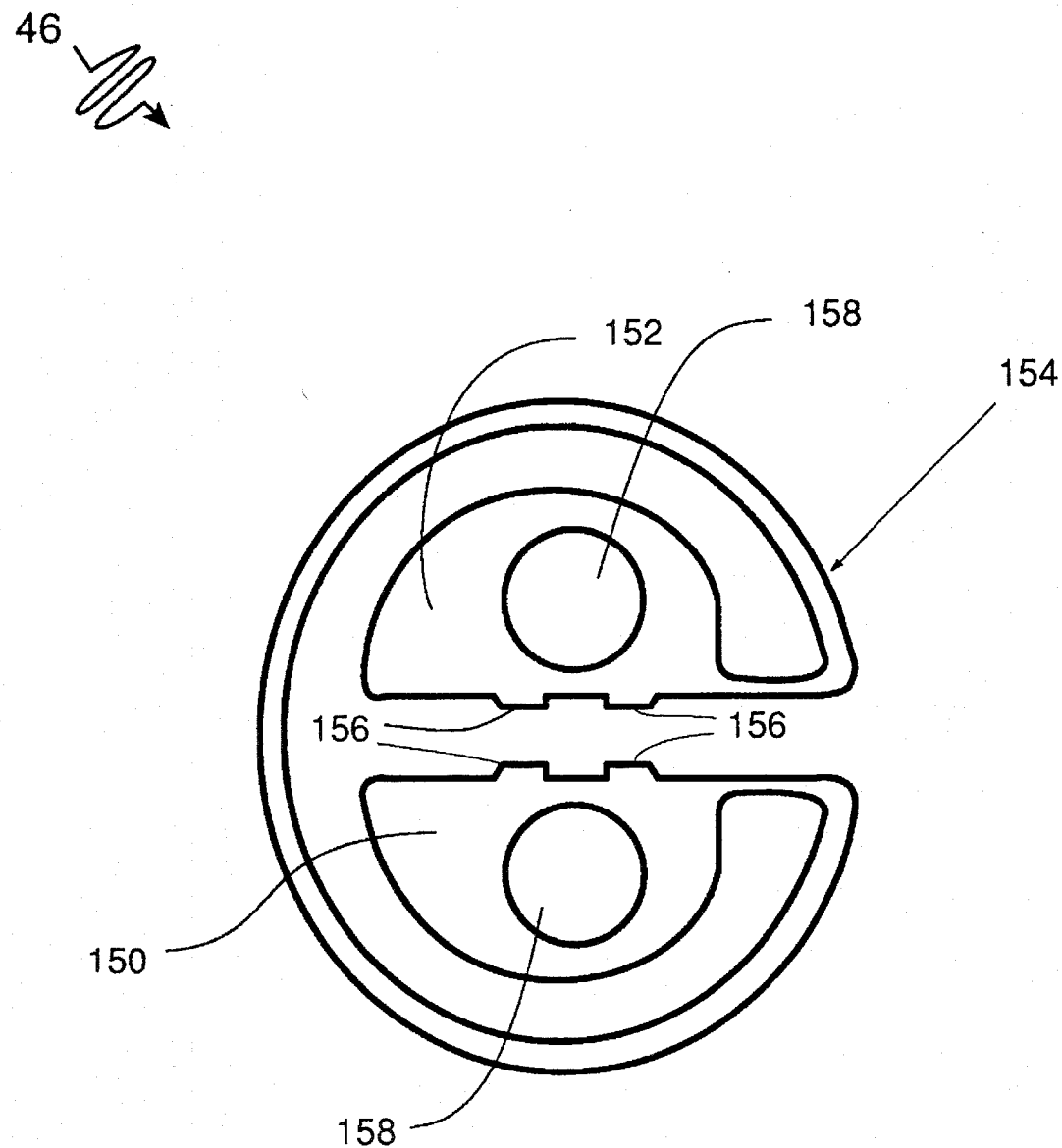
FIG. 6 is a plan view of the spring clip of the septum assembly of FIG. 1.

Clip 46 is designed as a spring closure for duckbill seal 44 to provide rapid closure as syringe needle 54 is removed and to provide reliable sealing even with low injection port pressure, as shown in FIG. 6. The overall geometry of clip 46 is circular and flat to allow it to fit in recess 128 without touching or binding except at lips 124. Clip 46 includes a pair of opposing pincers 150 and 152 which are flexibly connected by an arcuate ring 154, as shown in FIG. 6. Pincers 150 and 152 include tabs 156 to engage "T" stems 142. Apertures 158 in pincers 150 and 152 are designed to receive an insertion tool such as snap-ring pliers. The insertion tool forces pincers 150 and 152 apart until clip 46 is in position to engage "T" stems 142. The force is then relaxed to effect engagement and the insertion tool is removed.

Figure 7:
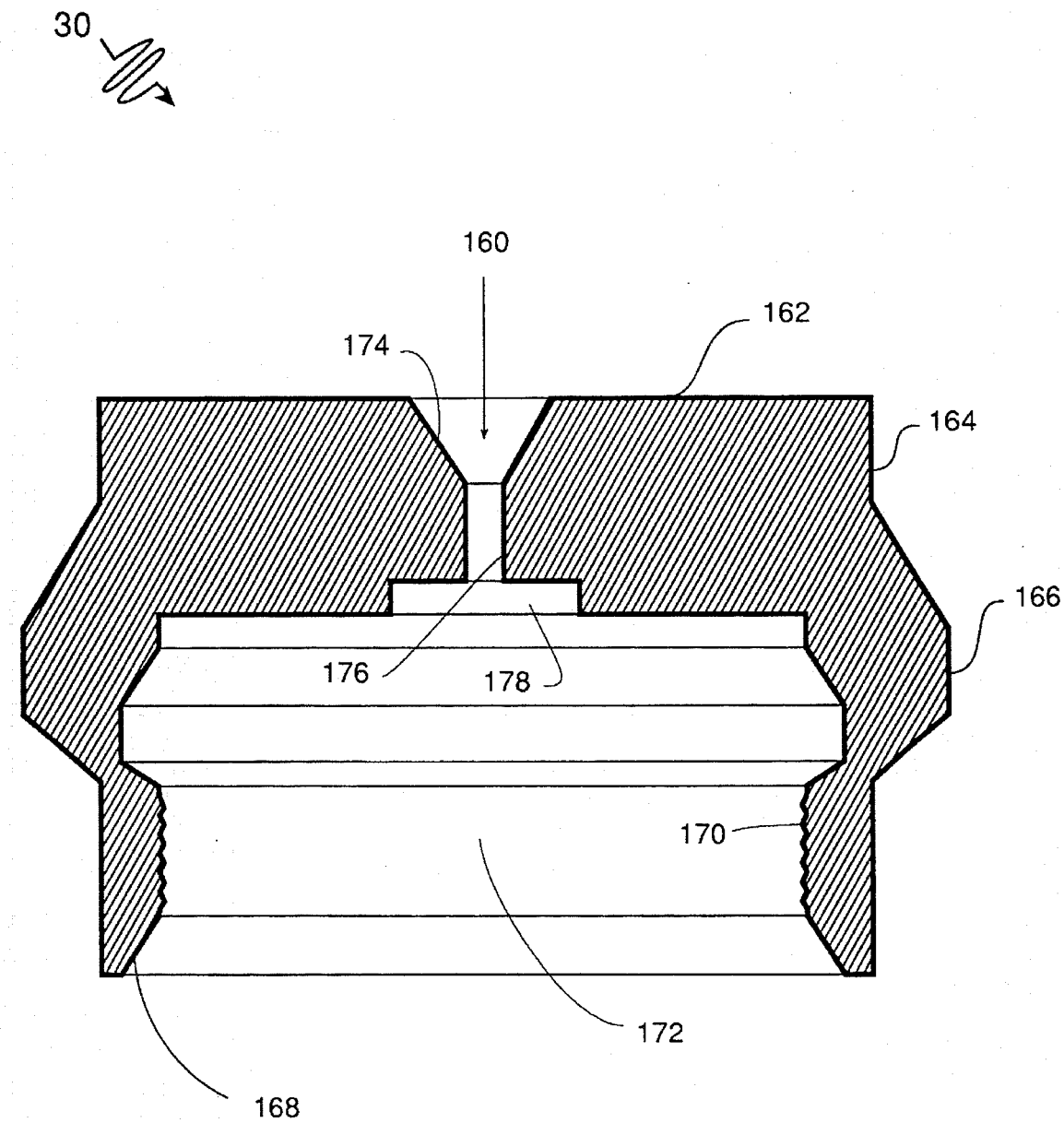
FIG. 7 is a sectional view of a septum nut of the septum assembly of FIG. 1.

Septum nut 30 serves to secure septum 40 in place in septum cup 28. Septum nut 30 includes a guide aperture 160, as shown in FIG. 7. When septum assembly 12 is secured on injection port 10, guide aperture 160 is aligned with syringe seal aperture 72 and duckbill aperture 100. Septum nut 30 has a generally smooth and radially symmetric shape. Its radially outward surface 164 is generally flat, with a hexagonal grip surface 166. A bottom ridge 168 is beveled to the interior to assist alignment prior to threading. On the interior, threads 170 provide for threaded engagement with the outer surface of septum cup 28. A large internal cavity 172 is large enough to receive septum cup 28, and thus septum 40.

Guide aperture 160 includes a generally conical capture section 174 and a cylindrical guide section 176. Guide section 176 extends from the narrow end of capture section 174 to a cylindrical recess 178. Recess 178 extends from guide section 176 to cavity 172. The purpose of guide section 176 is to guide needle 54 into syringe seal aperture 72. To this end, the inner diameter of guide section 176 should not exceed the outer needle diameter by more than 30%. Furthermore, the height-to-diameter aspect ratio of guide section 176 should be at least 2:1.

Capture section 174 is flared outward toward the top 162 of septum nut 30 to direct needle 54 into guide section 176. The minimum diameter of capture section 174 is the same as the diameter of guide section 176. The maximum diameter, at the top of capture section 174, should at least match the expected tolerance in the needle tip position at the time of insertion. Up to a point of diminishing returns, a greater maximum diameter is better. However, if the flare angle is excessive, needle 54 will gouge septum nut 30. Preferably, the flare has an internal angle of about 75° or less. The constraint on internal angle translates into a constraint on maximum flare diameter where an including system limits the height of septum nut 30. Such height constraints are found in certain auto-injection systems.

Recess 178 serves to collect dust wiped from needle 54 by wiping rib 94 so as to prevent or at least delay its entering syringe seal aperture 72. To this end, the diameter of recess 178 is greater than twice the diameter of guide section 176 and its height is at least one needle diameter. Washer 32 is locked in place to preclude deformation of septum 40 into recess 178.

Septum nut 30 differs considerably from its counterpart in U.S. Pat. No. 4,954,149 (septum nut 329). Instead of a full-length conical capture aperture, septum nut 30 includes shortened capture section 174 to allow room for guide section 176. Guide section 176 is required because, unlike the prior art syringe seal, syringe seal 42 has no flared-needle capture section. Since it is more difficult to drill guide section 176, which has a large aspect ratio, than it is to drill a flared section, septum nut 30 is fabricated from aluminum, rather than the hardened steel of the prior art septum nut. To offset some of the hardness lost by not using steel, the aluminum is anodized after guide aperture 160 is formed.

The dimensions of components and elements vary according to needle diameter, as well as other factors. 26- and 23-gauge needles are commonly used for sample injection. The following dimensions correspond to a 26-gauge (18.5 mil) injection needle.

The total height of the syringe aperture is 60 mil. The unstretched minimum diameters of the semi-toroidal wiping, strain-relief, and sealing elements are 16 mil. The center-to-center spacing between the sealing element and the strain-relief element is 10 mil, while the center-to-center spacing between the wiping element and the strain-relief element is 40 mil. These spacings are measures of the heights of the lower and upper dust pockets, respectively. The internal diameters of the dust pockets are 25 mil. The wiping element extends about 20 mil above the adjacent top surface of the syringe seal. The syringe seal outer diameter is 210 mil, with another 40 mil consumed by the 92° flap. The duckbill seal aperture depth is 155 mil, not including another 10 mil associated with duckbill upper-outer ridge 108. The maximum internal diameter for the duckbill seal, which matches the maximum external diameter of the syringe seal, is 490 mil.

The septum nut is about 500 mil high and about 685 mil in diameter. With added heat fins, not shown, the nut diameter is 1.13". The total depth of the septum nut aperture is 345 mil, with 149 being allocated to the conical capture section, 75 to the guide section, and 40 to the recess. The maximum diameter of the capture section is 240 mil; the internal flare angle is 75°. The guide section diameter is 21 mil, about 14% greater than the needle diameter. The recess diameter is 200 mil. The septum cavity diameter is 420 mil. The washer has an outer diameter of 390 mil and a height of 5 mil.

These dimensions can of course be varied to accommodate different needle dimensions, different injection port requirements, and other factors. These and other modifications to and variations upon the described embodiments are provided for by the present invention, the scope of which is limited only by the following claims.

What is claimed is:

1. A septum assembly for permitting injection of a fluid by extension of a needle therethrough, said needle having a needle diameter, said septum comprising:

an elastic duckbill seal having a duckbill aperture with a duckbill perimeter, said perimeter being at least as great as said needle diameter, said duckbill seal contacting and generally conforming to the cross section of said needle when said needle extends completely through said duckbill aperture, said duckbill aperture closing when said needle is withdrawn therefrom;

an elastic syringe seal having a generally annular aperture of varying diameter, said syringe seal mating with said duckbill seal so that said annular aperture and said duckbill aperture are aligned, said syringe seal having annular wipe, seal, and alignment elements, the diameters of said annular aperture at each of said elements being less than said needle diameter when said needle is not inserted therethrough, said wipe element being at an insertion end of said annular aperture, said seal element being at an opposite end of said aperture, said alignment element being between said wipe element and said seal element, said alignment element being closer to said seal element than to said wipe element, and annular wipe and seal pockets, the diameters of said annular aperture at each of said pockets being greater than said needle diameter when said needle is inserted through said annular aperture, said wipe pocket being between said wipe element and said alignment element, said seal pocket being between said seal element and said alignment element.

2. A septum assembly as recited in claim 1 further comprising a septum nut, said septum nut having threads for mating with a gas chromatography injection port, said septum nut being configured to mate with the mated combination of said duckbill seal and said syringe seal, said septum nut having a guide aperture aligned with said annular aperture and said duckbill aperture, said guide aperture having a cylindrical section with an inner diameter between 100% and 130% of said needle diameter, the height of said cylindrical section being at least twice its diameter.

3. A septum assembly as recited in claim 2 wherein said septum nut is of anodized aluminum.

4. A septum assembly as recited in claim 2 wherein said septum nut and said syringe seal are co-shaped so as to define near said wipe element a cavity for gathering particles removed from said needle by said wipe element, the volume not occupied by said septum of said cavity when said needle is inserted being at least the cube of said needle diameter.

5. A septum assembly as recited in claim 2 further comprising a washer disposed between said septum nut and said syringe seal so as to prevent protrusion of said syringe seal into said volume.

* * * * *